United States Patent
Morimoto

(10) Patent No.: US 12,092,809 B2
(45) Date of Patent: Sep. 17, 2024

(54) ILLUMINATION OPTICAL SYSTEM FOR ENDOSCOPE

(71) Applicant: FUJIFILM Corporation, Tokyo (JP)

(72) Inventor: Yoshinori Morimoto, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 307 days.

(21) Appl. No.: 17/670,679

(22) Filed: Feb. 14, 2022

(65) Prior Publication Data
US 2022/0171178 A1    Jun. 2, 2022

Related U.S. Application Data

(63) Continuation of application No. PCT/JP2020/028348, filed on Jul. 22, 2020.

(30) Foreign Application Priority Data

Aug. 27, 2019 (JP) ................ 2019-154577

(51) Int. Cl.
  *G02B 23/24* (2006.01)
  *A61B 1/07* (2006.01)
  *F21V 8/00* (2006.01)

(52) U.S. Cl.
  CPC ............ *G02B 23/2469* (2013.01); *A61B 1/07* (2013.01); *G02B 6/0008* (2013.01)

(58) Field of Classification Search
  CPC ...... G02B 23/2469; G02B 6/0008; A61B 1/07
  See application file for complete search history.

(56) References Cited

U.S. PATENT DOCUMENTS

| | | | |
|---|---|---|---|
| 8,721,152 B2* | 5/2014 | Coleman | F21S 8/06 362/555 |
| 8,838,213 B2* | 9/2014 | Tearney | A61B 5/0059 600/478 |
| 8,922,781 B2* | 12/2014 | Tearney | G01B 9/02091 356/479 |
| 9,295,391 B1* | 3/2016 | Tearney | A61B 1/07 |
| 9,415,550 B2* | 8/2016 | Tearney | G02B 23/2423 |
| 2004/0073120 A1* | 4/2004 | Motz | A61B 1/07 600/478 |

(Continued)

FOREIGN PATENT DOCUMENTS

| | | |
|---|---|---|
| JP | H08-122663 A | 5/1996 |
| JP | 2011-072424 A | 4/2011 |

(Continued)

OTHER PUBLICATIONS

International Search Report issued in PCT/JP2020/028348; mailed Oct. 6, 2020.

(Continued)

*Primary Examiner* — Bryon T Gyllstrom
(74) *Attorney, Agent, or Firm* — Studebaker & Brackett PC

(57) ABSTRACT

Provided is an illumination optical system for endoscope having high light utilization efficiency. The illumination optical system for endoscope which is provided in contact with an end surface of a light guide at a distal end portion of an insertion part of an endoscope, includes a diffusion plate that is provided on the end surface of the light guide and that diffuses light from the light guide, in which the diffusion plate has a diffusion surface that is formed on a surface on a side of the light guide and a light guide unit that guides light diffused on the diffusion surface, the diffusion surface consists of a holographic diffusion plate, and the light guide unit consists of sapphire glass.

21 Claims, 8 Drawing Sheets

(56) References Cited

U.S. PATENT DOCUMENTS

| | | | | |
|---|---|---|---|---|
| 2006/0114473 | A1* | 6/2006 | Tearney | A61B 5/0066 356/479 |
| 2010/0160734 | A1* | 6/2010 | Ivanovic | A61B 1/00096 600/122 |
| 2012/0051693 | A1 | 3/2012 | Yoshida et al. | |
| 2015/0015879 | A1* | 1/2015 | Papadopoulos | G02F 1/011 356/301 |
| 2016/0015467 | A1* | 1/2016 | Vayser | G02B 1/048 600/245 |
| 2019/0059701 | A1 | 2/2019 | Igarashi | |

FOREIGN PATENT DOCUMENTS

| | | |
|---|---|---|
| JP | 2012-050607 A | 3/2012 |
| JP | 2012-120635 A | 6/2012 |
| JP | 2012-139435 A | 7/2012 |
| JP | 2012-213562 A | 11/2012 |
| JP | 2012-232108 A | 11/2012 |
| JP | 2013-090674 A | 5/2013 |
| JP | 2015-223462 A | 12/2015 |
| WO | 2015/015996 A1 | 2/2015 |
| WO | 2017/217188 A1 | 12/2017 |

OTHER PUBLICATIONS

International Preliminary Report On Patentability and Written Opinion issued in PCT/JP2020/028348; issued Mar. 1, 2022.

The extended European search report issued by the European Patent Office on Sep. 30, 2022, which corresponds to European Patent Application No. 20857672.8-1020 and is related to U.S. Appl. No. 17/670,679.

* cited by examiner

ILLUMINATION OPTICAL SYSTEM FOR ENDOSCOPE

CROSS-REFERENCE TO RELATED APPLICATIONS

This application is a Continuation of PCT International Application No. PCT/JP2020/028348 filed on Jul. 22, 2020, which claims priority under 35 U.S.C. § 119(a) to Japanese Patent Application No. 2019-154577 filed on Aug. 27, 2019. The above application is hereby expressly incorporated by reference, in its entirety, into the present application.

BACKGROUND OF THE INVENTION

1. Field of the Invention

The present invention relates to an illumination optical system for endoscope.

2. Description of the Related Art

In an endoscope apparatus including a medical endoscope that is used to observe and treat the inside of a living body, an illumination window and an observation window are provided in a distal end of an endoscope insertion part, and illumination light is emitted from the illumination window and an observation image is acquired through the observation window. Light from, for example, a light source device such as a xenon lamp, a laser light source, and a light emitting diode (LED) is guided to the illumination window by a light guide such as an optical fiber, and is emitted from the illumination window.

An illumination optical system is disposed at a distal end portion of the light guide of the endoscope. In a case where the light guided by the light guide is emitted as it is, a range of a light emission angle is narrow and a light irradiation range is narrowed. Therefore, it has been performed that the illumination optical system is disposed at the distal end portion of the light guide to diffuse the light and expand the light irradiation range.

As such an illumination optical system, a system in which a plurality of lenses are combined, a system in which a member that diffuses light is disposed, and the like have been used.

For example, JP2012-213562A describes an endoscope apparatus provided with a function of detecting a light transmission loss, the endoscope apparatus comprising a first light source, a first light guide member that introduces output light of the first light source and guides the light to a distal end of an insertion part which is inserted into a subject, a wavelength conversion member that is disposed in a light emission end of the first light guide member, a second light source, a second light guide member that introduces output light of the second light source and guides the light to the distal end of the insertion part, a light diffusion member that is disposed in a light emission end of the second light guide member, a light source driving unit that generates a driving signal according to a target light amount set for each of the first and second light sources and drives the first and second light sources, a temperature sensor that detects a temperature of heat generated from the wavelength conversion member and the light diffusion member, a storage unit that stores a first temperature change rate caused by the heat generated from the wavelength conversion member corresponding to a driving signal intensity of the first light source and a second temperature change rate caused by the heat generated from the light diffusion member corresponding to a driving signal intensity of the second light source, and a light transmission loss detection unit that compares a third temperature change rate of a temperature detected by the temperature sensor, and the first temperature change rate and the second temperature change rate, that determines that a light transmission loss occurs in the second light guide member in a case where the third temperature change rate matches the first temperature change rate, and that determines that a light transmission loss occurs in the first light guide member in a case where the third temperature change rate matches the second temperature change rate.

Further, JP2012-232108A describes a light projecting unit for endoscope which is provided at a distal end portion of an endoscope and which irradiates a subject with illumination light, the light projecting unit for endoscope comprising a wavelength conversion member that absorbs a part of light having a predetermined wavelength, converts the wavelength to generate fluorescence, and transmits remaining light to emit illumination light including the light having the predetermined wavelength and the fluorescence, and a spread angle enlarging unit that scatters the illumination light emitted from the wavelength conversion member and enlarges a spread angle of the illumination light. JP2012-232108A describes that the spread angle enlarging unit is a member in which a filler is mixed into a resin.

SUMMARY OF THE INVENTION

According to the study by the inventors, it has been found that light utilization efficiency is not sufficient in a case where light guided by a light guide and emitted is diffused by using a diffusion member in which a filler is mixed into a resin, as described in JP2012-232108A. Low light utilization efficiency causes a problem that an amount of heat generated becomes large.

Specifically, since the filler is an isotropic scattering material, light incident on the filler is diffused in all directions. Therefore, a large amount of light is scattered in a direction other than an emission direction, and the efficiency is decreased. It has also been performed that a reflection plate is provided on a surface except an emission surface and the light scattered in the direction other than the emission direction is made to be reflected, but the light strikes the filler again and is isotropically scattered. Although the light is emitted to an outside by repeating the reflection by the reflection plate and the isotropic scattering by the filler, the efficiency is deteriorated because the reflection and the scattering are repeated many times.

An object of the present invention is to solve the above-described problem based on the prior art and to provide an illumination optical system for endoscope having high light utilization efficiency.

In order to achieve the object, the present invention has the following configuration.

[1] An illumination optical system for endoscope which is provided in contact with an end surface of a light guide at a distal end portion of an insertion part of an endoscope, the illumination optical system for endoscope comprising:
  a diffusion plate that is provided on the end surface of the light guide and diffuses light from the light guide,
  in which the diffusion plate has a diffusion surface that is formed on a surface on a side of the light guide and a light guide unit that guides light diffused on the diffusion surface,
  the diffusion surface consists of a holographic diffusion plate, and the light guide unit consists of sapphire glass.

[2] The illumination optical system for endoscope according to [1], in which an emission surface of the light guide unit on a side opposite to the diffusion surface includes the end surface of the light guide when viewed from a direction perpendicular to a surface of the light guide unit of the diffusion plate on the side opposite to the diffusion surface, and in a case where a shortest distance between an edge side of the emission surface and an edge side of the end surface of the light guide, in an in-plane direction of the emission surface, is denoted by L, and a thickness of the diffusion plate in a direction perpendicular to the emission surface is denoted by t, t/L≤1.6 is satisfied.

[3] The illumination optical system for endoscope according to [2], in which the shortest distance L and the thickness t satisfy 0.5≤t/L≤1.6.

[4] The illumination optical system for endoscope according to [2] or [3], in which the thickness t is 0.2 mm or more and 0.5 mm or less.

[5] The illumination optical system for endoscope according to any one of [1] to [4], in which a diffusion angle at half maximum of the diffusion plate is 30° or more.

[6] The illumination optical system for endoscope according to any one of [1] to [5], in which a light distribution angle of the light guide is 80° or more.

[7] The illumination optical system for endoscope according to any one of [1] to [6], in which a side surface of the light guide unit is bonded by an adhesive or is brazed to the distal end portion of the insertion part of the endoscope.

[8] The illumination optical system for endoscope according to any one of [1] to [7], in which an emission surface of the light guide unit has a circular shape when viewed from a direction perpendicular to the emission surface of the light guide unit of the diffusion plate, and the end surface of the light guide has a circular shape.

[9] The illumination optical system for endoscope according to [8], in which the end surface of the light guide has a diameter of 0.5 mm to 2.0 mm.

[10] The illumination optical system for endoscope according to any one of [1] to [9], in which an emission surface of the light guide unit is in contact with an air layer.

According to the present invention, it is possible to provide an illumination optical system for endoscope having high light utilization efficiency.

DESCRIPTION OF THE PREFERRED EMBODIMENTS

Hereinafter, an illumination optical system for endoscope of an embodiment of the present invention will be described in detail on the basis of a preferred embodiment shown in the accompanying drawings.

It should be noted that the drawings described below are examples illustrating the present invention, and the present invention is not limited to the drawings shown below.

In the following, "to" indicating the numerical range includes the numerical values described on both sides thereof. For example, in a case where ε is a numerical value α to a numerical value β, the range of ε is a range including the numerical value α and the numerical value β, and is represented by α≤ε≤β in mathematical symbols.

In addition, "whole surface" and the like include an error range generally allowed in the relevant technical field.

The illumination optical system for endoscope of the embodiment of the present invention is an illumination optical system for endoscope which is provided in contact with an end surface of a light guide at a distal end portion of an insertion part of an endoscope, the illumination optical system for endoscope comprising:

a diffusion plate that is provided on the end surface of the light guide and diffuses light from the light guide, in which the diffusion plate has a diffusion surface that is formed on a surface on a side of the light guide and a light guide unit that guides light diffused on the diffusion surface, the diffusion surface consists of a holographic diffusion plate, and the light guide unit consists of sapphire glass.

[Endoscope System]

First, an endoscope system having an endoscope having the illumination optical system for endoscope of the embodiment of the present invention will be described.

Figure 1:
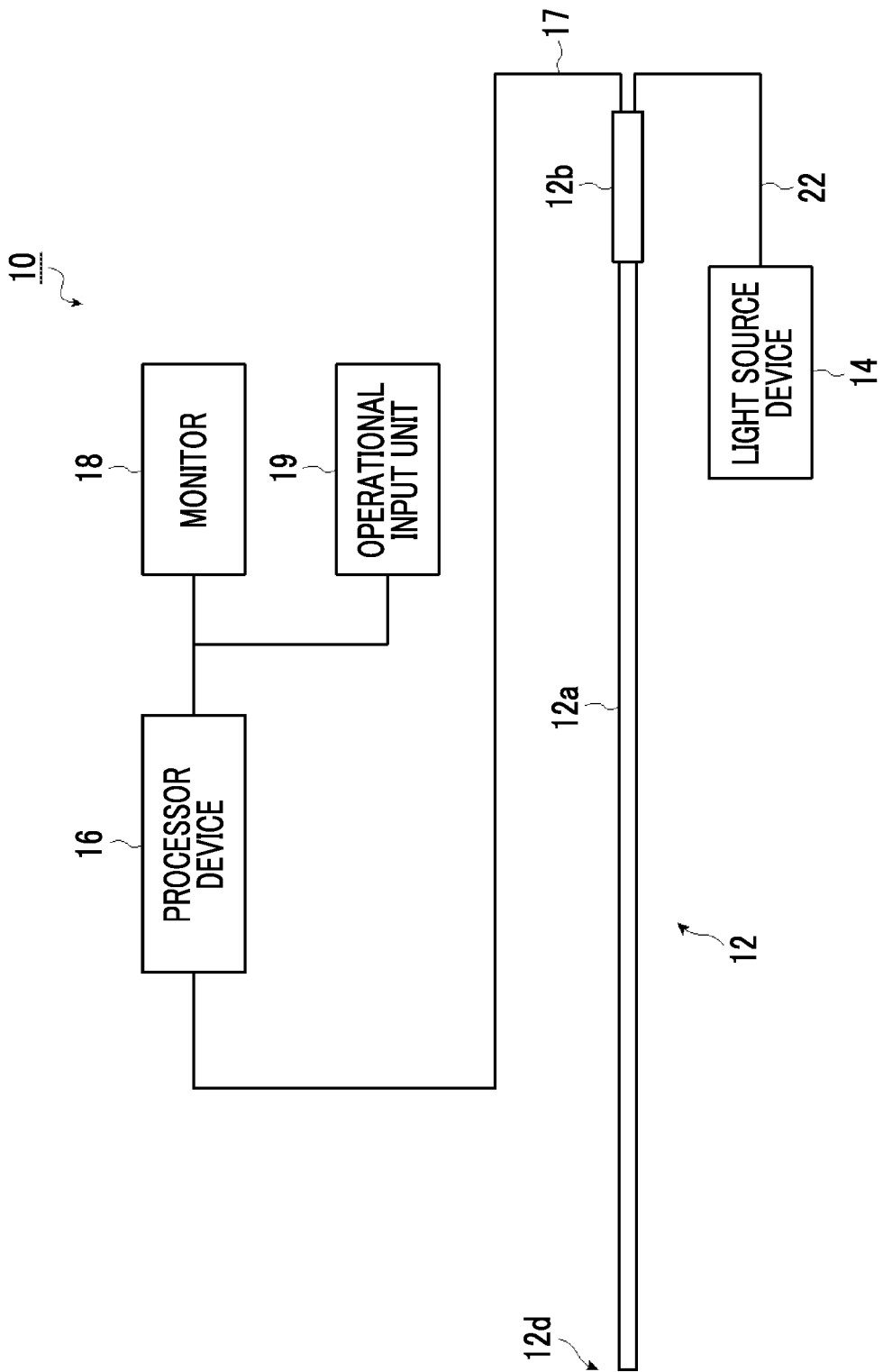
FIG. 1 is a schematic view showing an example of an endoscope system having an illumination optical system for endoscope of an embodiment of the present invention.

FIG. 1 is a schematic view showing an example of the endoscope system having the endoscope having the illumination optical system for endoscope of the embodiment of the present invention.

An endoscope system 10 irradiates an observation site in a living body (inside a subject), which is an observation target, with illumination light, picks up an image of the observation site, generates a display image of the observation site on the basis of an image signal obtained by the image pick-up, and displays the display image.

The endoscope system 10 has the same configuration as a conventionally known endoscope system except that the endoscope system 10 has the illumination optical system for endoscope of the embodiment of the present invention.

As shown in FIG. 1, the endoscope system 10 comprises an endoscope 12 that picks up an image of an observation site in a living body (inside a subject), which is an observation target, a processor device 16 that generates a display image of the observation site on the basis of an image signal obtained by the image pick-up, a light source device for endoscope (hereinafter, simply referred to as a light source device) 14 that supplies illumination light with which the observation site is irradiated, to the endoscope 12, and a monitor 18 that displays the display image. An operational input unit 19, such as a keyboard and a mouse, is connected to the processor device 16.

The endoscope 12 comprises an insertion part 12a that is inserted into the subject, such as the inside of a body of a patient, and an operation part 12b provided at a proximal end portion of the insertion part 12a. In the endoscope 12, a side of the insertion part 12a is a side of the distal end. The operation part 12b of the endoscope 12 is connected to the processor device 16 via a signal line 17. The endoscope 12 is, for example, a forward-viewing type rigid endoscope, such as a laparoscope.

The processor device 16 receives the image signal output from an image pick-up unit of the endoscope 12 via the signal line 17, generates a video signal, and outputs the video signal to the monitor 18. By doing so, the display image of the observation site, such as the inside of the body, is displayed on the monitor 18.

The operation part 12b of the endoscope 12 is connected to the light source device 14 via a light guide 22. Light from the light source device 14 is supplied to the light guide 22, and the light is emitted from a distal end of the endoscope 12.

Figure 2:
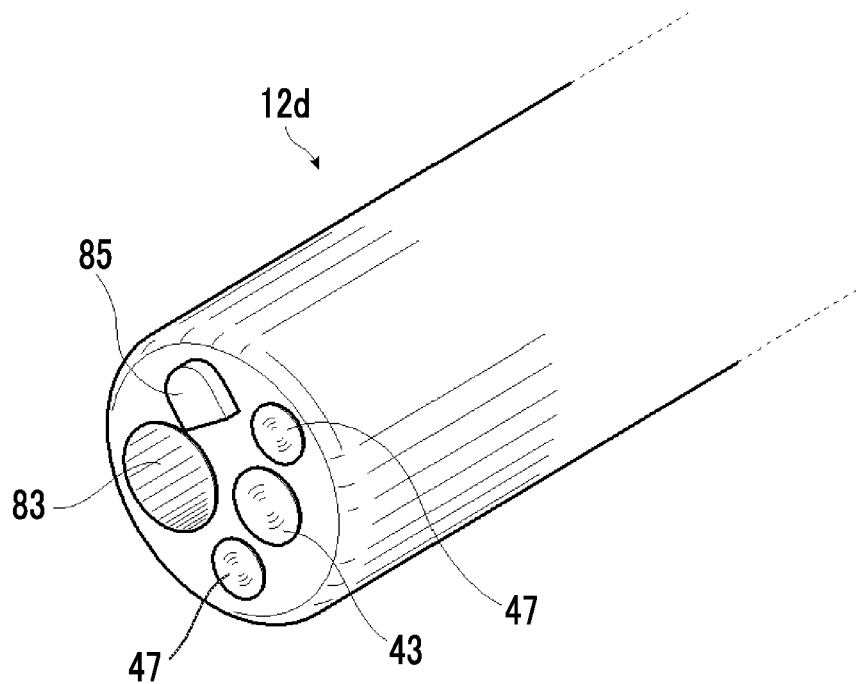
FIG. 2 is a perspective view schematically showing a distal end portion of an endoscope having the illumination optical system for endoscope of the embodiment of the present invention.

FIG. 2 shows an enlarged perspective view of a distal end portion 12d of the endoscope 12.

As shown in FIG. 2, in the distal end portion 12d (distal end surface) of the endoscope 12, as an example, an observation window 43 of an image pick-up optical system, an illumination window 47 of an illumination optical system, a forcep channel 83, and an air and water supply channel that communicates with an air and water supply nozzle 85 are disposed. In the example shown in FIG. 2, two illumination windows 47 are provided, and the two illumination windows 47 are disposed on both sides of the observation window 43 interposed therebetween.

The illumination optical system for endoscope of the embodiment of the present invention is disposed in such an illumination window 47, propagates the light guided by the light guide 22, and emits the light from the illumination window.

[Illumination Optical System for Endoscope]

Figure 3:
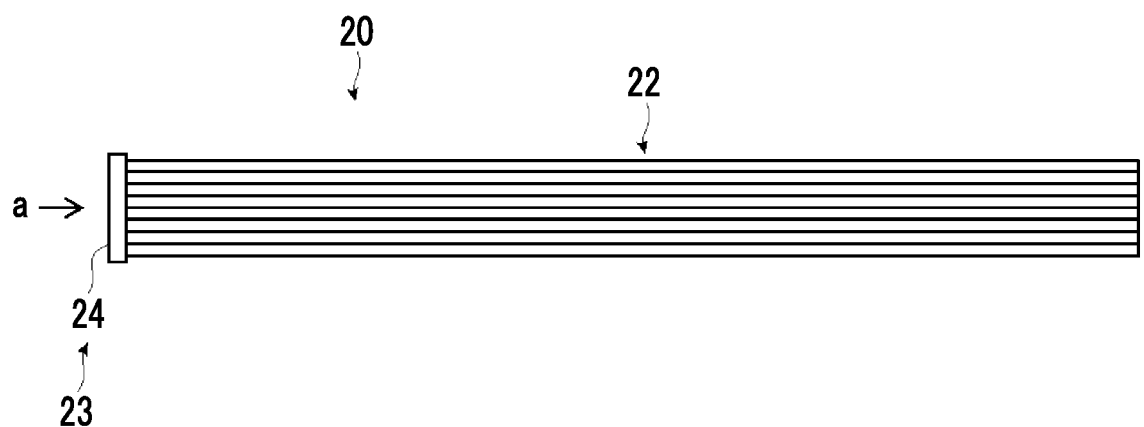
FIG. 3 is a side view schematically showing an illumination unit having the illumination optical system for endoscope of the embodiment of the present invention.

FIG. 3 shows a side view schematically showing an illumination unit having the light guide and the illumination optical system for endoscope of the embodiment of the present invention.

An illumination unit 20 shown in FIG. 3 has the light guide 22 and an illumination optical system for endoscope 23 disposed on an end surface of the light guide 22.

The light guide 22 is a light transmission member, and is formed of, for example, a bundle of a plurality of optical fiber strands. As described above, the light guide 22 guides the light supplied from the light source device 14 and emits the light from the end surface of the light guide 22. Since the illumination optical system for endoscope 23 is disposed on the end surface of the light guide 22, the light emitted from the end surface of the light guide 22 is incident on the illumination optical system for endoscope 23.

Figure 4:
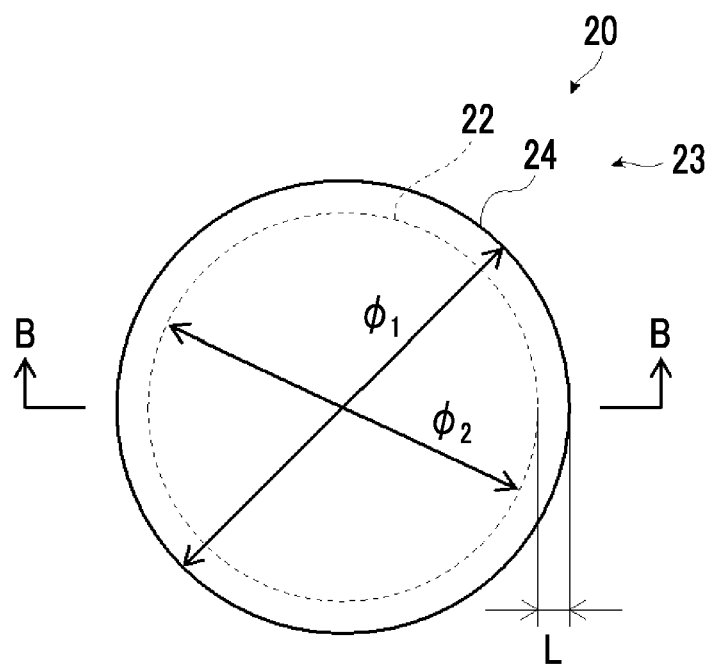
FIG. 4 is a top view of the illumination unit shown in FIG. 3 as viewed from an a direction.
Figure 5:
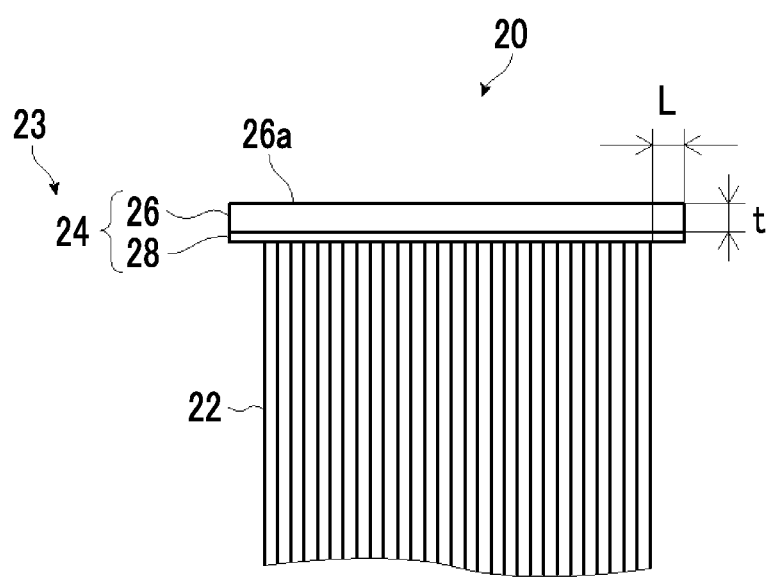
FIG. 5 is a cross-sectional view taken along a line B-B of FIG. 4.

FIG. 4 shows a top view of the illumination unit 20 of FIG. 3 as viewed from an a direction, and FIG. 5 shows a cross-sectional view taken along a line B-B of FIG. 4.

As shown in FIGS. 4 and 5, the illumination optical system for endoscope 23 has a diffusion plate 24.

The diffusion plate 24 is used to diffuse the light emitted from the end surface of the light guide 22 and to widen a light irradiation range.

As shown in FIG. 5, the diffusion plate 24 has a light guide unit 26 and a diffusion surface 28.

The diffusion surface 28 is formed on a surface of the diffusion plate 24 on a side in contact with the light guide 22. The diffusion surface 28 consists of a holographic diffusion plate, and diffuses and transmits the light emitted from the end surface of the light guide 22.

The holographic diffusion plate has a surface uneven structure formed so that the reproduced light becomes diffused light that is diffused in any angle range. As an example, the shape is as shown in FIG. 10(a) of Holographic diffuser by use of a silver halide sensitized gelatin process, APPLIED OPTICS Vol. 42, No. 14, 10 May, 2003.

With the holographic diffusion plate having such a surface uneven structure, the light emitted from the light guide 22 is diffused in a predetermined angle range.

In the present invention, the light guide unit 26 is used as a substrate and a holographic diffusion plate is formed on the light guide unit 26.

A method for forming the holographic diffusion plate is not particularly limited, and a conventionally known forming method can be used.

For example, the sol-gel method can be used to form the holographic diffusion plate. Specifically, a solution (sol) containing $SiO_2$, which is a material of the holographic diffusion plate, is prepared, applied on the substrate, and then gelled, and in a state in which a master (mold) to which the surface uneven structure designed by the computer-generated hologram can be transferred is pressed against the gelled coating film, the coating film is heated and cured, so that the holographic diffusion plate can be formed.

Glass can be used as the substrate for the holographic diffusion plate. The material of the holographic diffusion plate is a composite material including glass.

The light diffused on the diffusion surface 28 is incident on the light guide unit 26.

The light guide unit 26 is a plate-shaped member that guides the light diffused on the diffusion surface 28 and that emits the light from an emission surface 26a on a side opposite to a surface on which the diffusion surface 28 is formed. The light guide unit 26 consists of sapphire glass having a high refractive index, and when light is emitted from the emission surface 26a, refracts the light at the interface due to a difference in refractive index from the outside to further widen the light irradiation range. Specifically, the refractive index of sapphire glass is about 1.77. For example, the emission surface 26a is in contact with an air layer, and when light is emitted from the emission surface 26a, the light is refracted at the interface with the air layer due to a relationship with the refractive index of air (n=1).

Further, the sapphire glass has a Vickers hardness of about 22.5 GPa, which is very hard. Therefore, the thickness of the light guide unit 26 can be reduced.

The thickness of the diffusion plate 24 (the light guide unit 26+the diffusion surface 28) is preferably 200 μm to 500 μm, more preferably 200 μm to 400 μm, and even more preferably 200 μm to 300 μm. Since the thickness of the diffusion surface 28 (holographic diffusion plate) is very thin, the thickness of the light guide unit 26 can be approximated to the thickness of the diffusion plate 24.

In the example shown in FIG. 4, the end surface of the light guide 22 has a circular shape when viewed from a direction perpendicular to the emission surface 26a of the light guide unit 26 of the diffusion plate 24 on a side opposite to the diffusion surface 28, that is, when viewed from an a direction in FIG. 3. Further, the emission surface 26a when viewed from the direction perpendicular to the emission surface 26a also has a circular shape. Further, the center of the end surface of the light guide 22 and the center of the emission surface 26a, when viewed from the direction perpendicular to the emission surface 26a are disposed so as to match each other.

Further, the diameter $\varphi_1$ of the emission surface 26a is larger than the diameter $\varphi_2$ of the end surface of the light guide 22.

Therefore, in the example shown in FIG. 4, the emission surface 26a includes the end surface of the light guide 22 when viewed from the direction perpendicular to the emission surface 26a.

Here, in the present invention, in a case where a shortest distance between the edge side of the emission surface 26a and the edge side of the end surface of the light guide 22, in the in-plane direction of the emission surface 26a, is denoted by L, and the thickness of the diffusion plate 24 in the direction perpendicular to the emission surface 26a is denoted by t, it is preferable that t/L≤1.6 is satisfied. In the example shown in FIG. 4, the shortest distance L is ($\varphi_1$-$\varphi_2$)/2.

The action of the illumination optical system for endoscope having such a configuration will be described with reference to FIGS. 6 to 11.

Figure 6:
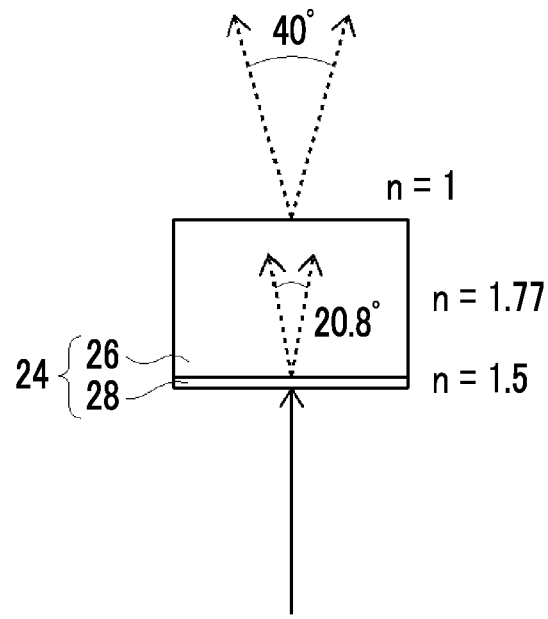
FIG. 6 is a diagram illustrating an action of a diffusion plate.
Figure 7:
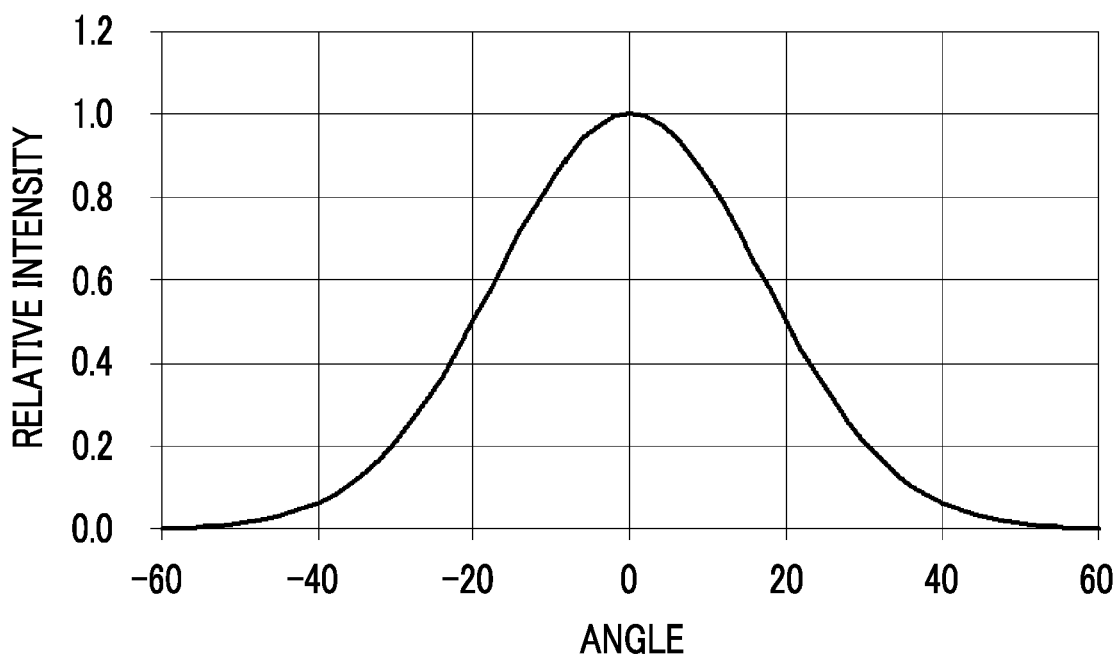
FIG. 7 is a graph showing an angular distribution of light in a light guide unit.

First, a case where light is incident on the diffusion plate 24 perpendicularly to the surface of the diffusion surface 28 from a side of the diffusion surface 28 is considered. As shown in FIG. 6, the incident light is diffused by the diffusion surface 28 and is guided while spreading in the light guide unit 26. FIG. 7 shows the diffused light and the angular distribution in the light guide unit 26. In the distribution shown in FIG. 7, the light intensity (relative intensity) in a direction of an angle of 0° (vertical direction) is highest, and the intensity is decreased as the angle is increased. In FIGS. 6 and 7, as an example, a full angle at half maximum of the intensity of the light diffused on the diffusion surface 28 is 20.8°.

Figure 8:
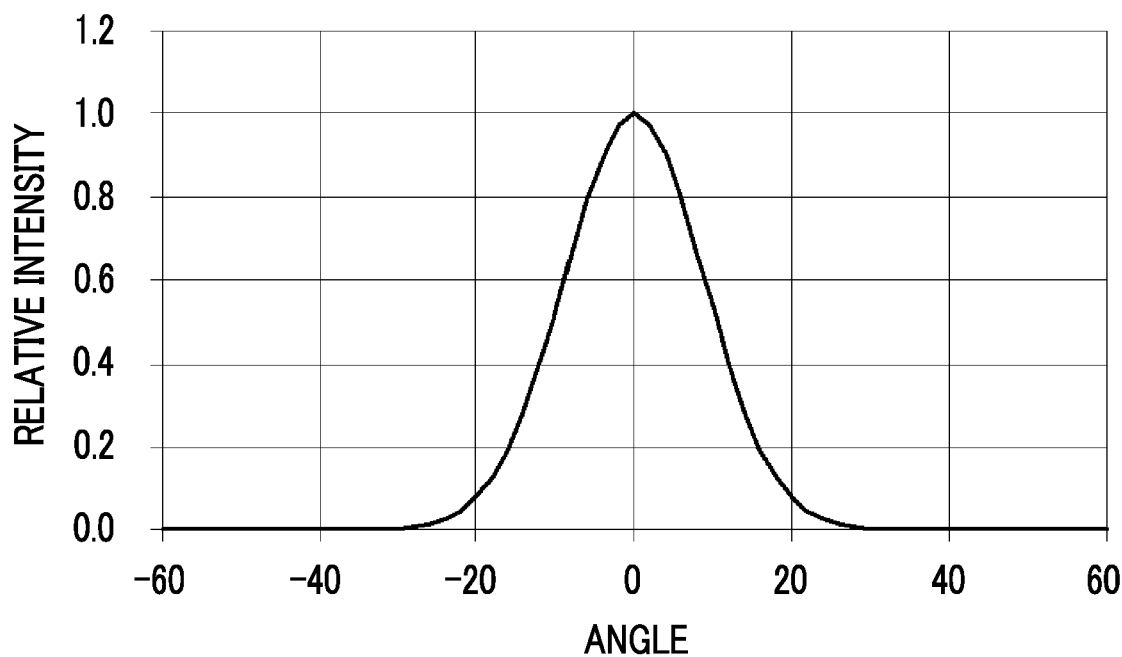
FIG. 8 is a graph showing an angular distribution of light emitted from the diffusion plate.

In a case where the light diffused on the diffusion surface 28 is emitted from the light guide unit 26, the light is refracted in response to the difference in refractive index from the outside (air), and is emitted. Therefore, as shown in FIG. 6, the light is emitted with a further spread. FIG. 8 shows the angular distribution of the light emitted from the light guide unit 26. In the examples shown in FIGS. 6 and 8, the full angle at half maximum of the intensity of the light emitted from the light guide unit 26 is 40°.

In this way, the diffusion plate 24 can emit light having an angular distribution due to the light diffusion on the diffusion surface 28 and the refraction when light is emitted from the light guide unit 26.

Figure 9:
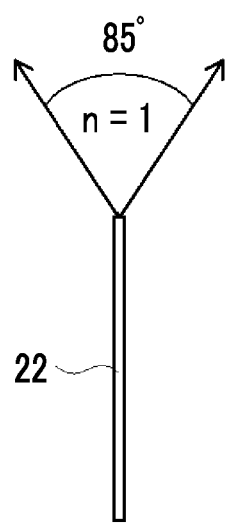
FIG. 9 is a diagram illustrating a light distribution angle of a light guide.

Next, the light emitted from the light guide will be described. As shown in FIG. 9, the light emitted from the light guide 22 is emitted at a predetermined light distribution angle. For example, in a case where light is emitted into the air (n=1), the light distribution angle of the light emitted from the light guide is 85°.

Figure 10:
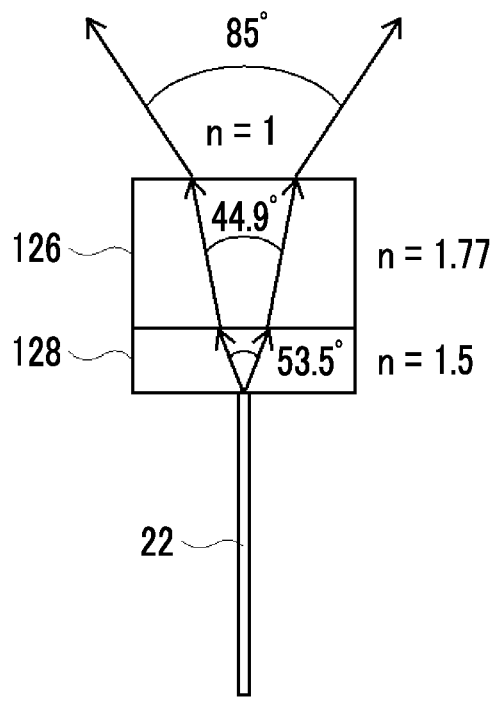
FIG. 10 is a diagram illustrating the light distribution angle of the light guide.

Here, a case where the end surface of the light guide 22 has layers having different refractive indexes is considered. For example, as shown in FIG. 10, in a case where a first layer 128 (corresponding to a diffusion surface 28 having no diffusivity) having a refractive index of 1.5 is disposed on the end surface of the light guide 22, and a second layer 126 (corresponding to the light guide unit 26) having a refractive index of 1.77 is disposed on the surface of the first layer 128, light emitted from the end surface of the light guide becomes light having a light distribution angle of 53.5° due to the difference in refractive index between the light guide 22 and the first layer 128, and is guided into the first layer 128 and reaches the second layer 126. In a case where the light is incident on the second layer 126 from the first layer 128, the light becomes light having a light distribution angle of 44.9° due to the difference in refractive index between the first layer 128 and the second layer 126, and is guided into the second layer 126 and is emitted from the surface of the second layer 126. In a case where the light is emitted from the surface of the second layer 126, the light becomes light having a light distribution angle of 85° due to the difference in refractive index between the second layer 126 and the air, and is emitted. That is, the light distribution angle of the light that is emitted into the air is the same as the light distribution angle of the light that is directly emitted from the light guide even in a case where another layer is provided between the end surface of the light guide 22 and the air layer.

Since the diffusion surface 28 (holographic diffusion plate) consists of a composite material containing glass, the refractive index is about 1.5.

Figure 11:
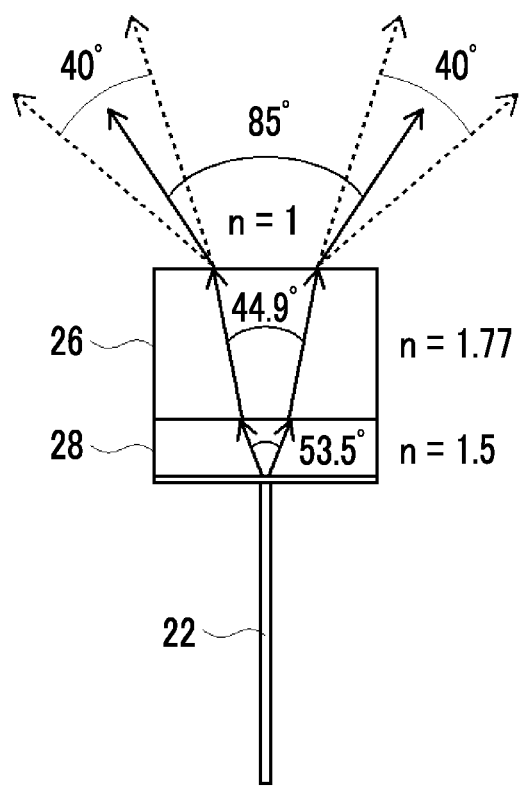
FIG. 11 is a diagram illustrating an action of the illumination optical system for endoscope of the embodiment of the present invention.

As in the present invention, in a case where the diffusion plate 24 having a function of diffusing light is disposed on the end surface of the light guide 22, as shown in FIG. 11, the above-described light distribution characteristics of the light guide 22 and the scattering characteristics of the diffusion plate 24 are integrated to determine the light distribution characteristics of the emitted light.

As described above, with the illumination optical system for endoscope of the embodiment of the present invention using the diffusion plate 24 having the diffusion surface 28 and the light guide unit 26, the irradiation range of the emitted light can be made wider than the light distribution angle of the light that is directly emitted from the light guide.

In the example shown in FIG. 11 and the like, the spread angle of the light caused by diffusion is 40°, but as shown in FIG. 8, the angle is a full angle at half maximum, and light irradiation can actually be performed in a wider angle range. For example, in the example shown in FIG. 8, the angle at which the light intensity is about 5% is about ±42°. Therefore, in a case where the light distribution characteristics of the light guide 22 are combined, irradiation with light having an intensity of 5% or more can be performed in a range of about 170°.

Figure 12:
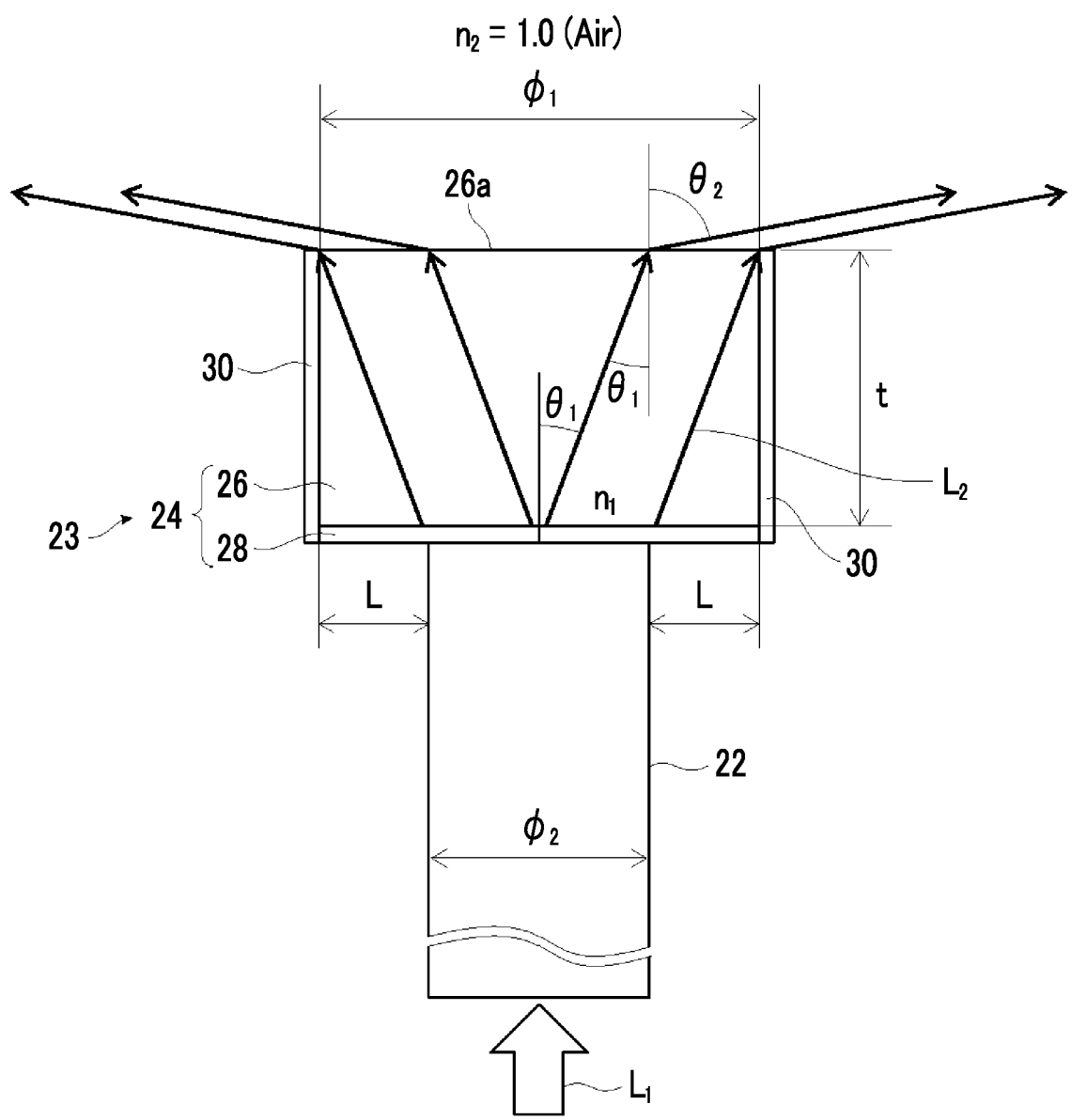
FIG. 12 is a diagram illustrating a relationship between a shortest distance L between an edge side of an emission surface and an edge side of an end surface of the light guide, and a thickness t of the light guide unit.

Here, as shown in FIG. 12, the maximum emission angle $\theta_2$ of the light emitted from the distal end of the endoscope need only be about 85°.

The incident angle $\theta_1$ in a case where the emission angle $\theta_2$ of the light emitted from the illumination optical system for endoscope of the embodiment of the present invention is 85°, is calculated as $\theta_1$=34.3° from the refractive index $n_1$=1.77 of the sapphire glass and the refractive index $n_2$=1.0 of the air layer.

As shown by $L_2$ in FIG. 12, in a case where the light $L_2$ emitted from a position of the edge side of the end surface of the light guide 22 and incident on the diffusion plate 24 is emitted at a position of the edge side of the emission surface 26a, $t/L=1/\tan\theta_1$ is satisfied. As described above, the incident angle $\theta_1$ at which the emission angle $\theta_2$ of the light emitted from the emission surface 26a is 85° is 34.3°, so that t/L is 1.47.

In a case where t/L is larger than 1.6, the light that is guided into the light guide unit 26 reaches the side surface of the light guide unit 26. Since the side surface of the light guide unit 26 is bonded to the distal end portion of the insertion part of the endoscope by, for example, an adhesive 30 or brazing, the light that has reached the side surface of the light guide unit 26 is not totally reflected and is absorbed by the adhesive 30 or the like. Therefore, the amount of light emitted from the emission surface 26a is decreased, and the light utilization efficiency is decreased.

On the other hand, in the present invention, with $t/L \leq 1.6$ satisfied, it is possible to prevent the light incident on the diffusion plate 24 from the light guide 22 from reaching the side surface of the light guide unit 26, and from being absorbed on the side surface by the adhesive 30 or the like, so that it is possible to prevent the decrease in light utilization efficiency. In addition, since the light utilization efficiency can be increased, it is possible to restrain the increase in the amount of heat generated.

Here, in a case where the diameter $\varphi_2$ of the light guide 22 is fixed, it is necessary that the thickness t of the diffusion plate 24 is reduced and/or the diameter $\varphi_1$ of the emission surface 26a of the diffusion plate 24 is increased.

Since it is desired that the distal end portion of the endoscope is made thin, it is difficult to increase the diameter $\varphi_1$ of the emission surface 26a of the diffusion plate 24. Meanwhile, in a case where the thickness t of the diffusion plate 24 is reduced, durability such as cracking of the diffusion plate 24 becomes a problem.

In response to this, in the present invention, sapphire glass having high hardness is used for the light guide unit 26 of the diffusion plate 24, so that cracking can be restrained even in a case where the thickness t is reduced. Therefore, the diffusion plate 24 can be made smaller and thinner. Further, with the light guide unit 26 made thinner, it is possible to restrain the decrease in utilization efficiency caused by the occurrence of light loss in the light guide unit 26.

In a case where the end surface of the light guide 22 has a circular shape, the diameter $\varphi_2$ of the end surface is preferably 0.5 mm to 2.0 mm from the viewpoint of ensuring the flexibility of the endoscope insertion part by which light from the light source device can be guided with high efficiency.

The light distribution angle of the light emitted from the end surface of the light guide 22 is preferably 80° or more.

Here, the light distribution angle is the spread angle of the light when the light is emitted into the air from the end surface of the light guide 22.

The diffusion angle at half maximum (full angle at half maximum of the diffused light) of the diffusion plate 24 is preferably 30° or more.

Here, the diffusion angle at half maximum is the full angle at half maximum of the diffused light described with reference to FIG. 6.

Here, in the examples shown in FIGS. 4 and 5, the end surface of the light guide 22 has a circular shape, but the present invention is not limited thereto. The shape of the end surface of the light guide 22 can be any shape such as an elliptical shape, a polygonal shape, and an amorphous shape.

Similarly, the emission surface 26a of the diffusion plate 24 has a circular shape, but the present invention is not limited thereto. The shape of the emission surface 26a of the diffusion plate 24 can be any shape such as an elliptical shape, a polygonal shape, and an amorphous shape.

In the examples shown in FIGS. 4 and 5, the shape of the end surface of the light guide 22 and the shape of the emission surface 26a of the diffusion plate 24 are similar to each other, but the present invention is not limited thereto, and the shapes may be different from each other.

Further, in the examples shown in FIGS. 4 and 5, the center of the end surface of the light guide 22 and the center of the emission surface 26a of the diffusion plate 24 are disposed so as to match each other in the plane direction, but the present invention is not limited thereto, and the center of the end surface of the light guide 22 and the center of the emission surface 26a of the diffusion plate 24 may deviate from each other.

Figure 13:
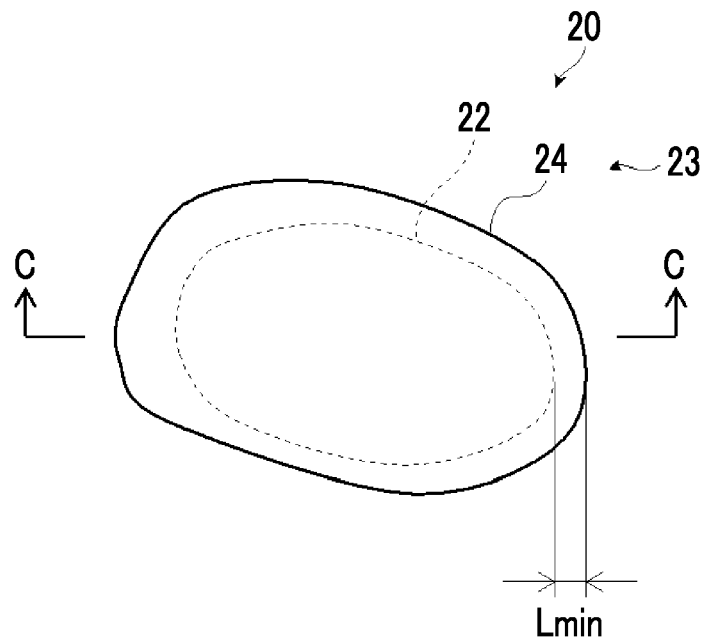
FIG. 13 is a top view schematically showing an illumination unit having another example of the illumination optical system for endoscope of the embodiment of the present invention.
Figure 14:
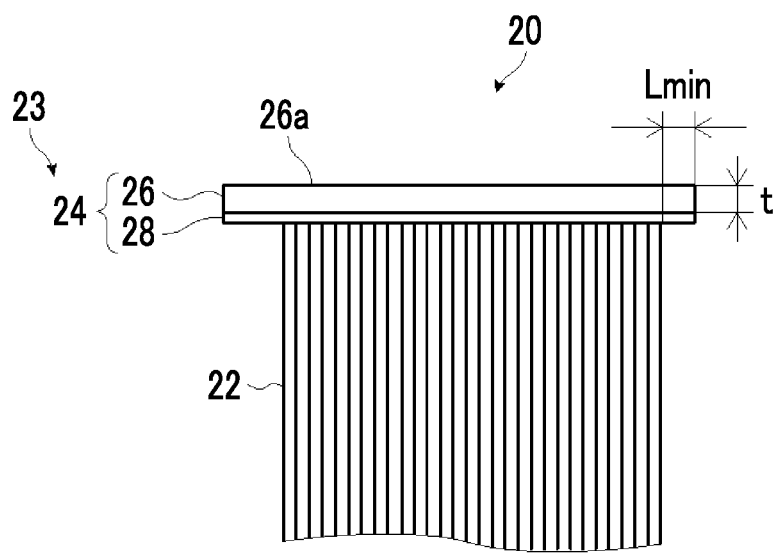
FIG. 14 is a cross-sectional view taken along a line C-C of FIG. 13.

For example, FIGS. 13 and 14 show an example of an illumination unit having another example of the illumination optical system for endoscope of the embodiment of the present invention.

FIG. 13 is a top view of the illumination unit, and FIG. 14 is a cross-sectional view taken along a line C-C of FIG. 13.

In the example shown in FIG. 13, each of the end surface of the light guide 22 and the emission surface 26a of the diffusion plate 24 has an amorphous shape. Further, the end surface of the light guide 22 and the emission surface 26a of the diffusion plate 24 have a non-similar shape to each other. Further, the center of the end surface of the light guide 22 and the center of the emission surface 26a of the diffusion plate 24 do not match each other. Further, in the example shown in FIG. 8, the emission surface 26a includes the end surface of the light guide 22 when viewed from the direction perpendicular to the emission surface 26a.

In the case of the configuration shown in FIGS. 13 and 14, the distance between the edge side of the emission surface 26a and the edge side of the end surface of the light guide 22, in the in-plane direction of the emission surface 26a, differs depending on the position, but in the present invention, a distance at a position where the distance between the edge side of the emission surface 26a and the edge side of the end surface of the light guide 22 is shortest, and in the examples shown in FIGS. 13 and 14, a distance at a position where the distance is Lmin need only be set as the shortest distance L.

Although the illumination optical system for endoscope of the embodiment of the present invention has been described in detail above, the present invention is not limited to the above-described embodiment, and needless to say, various modifications or changes may be made without departing from the gist of the present invention.

EXAMPLES

Hereinafter, the present invention will be described in more detail with reference to specific examples of the present invention.

Example 1

An illumination unit having an illumination optical system for endoscope as shown in FIGS. 4 and 5 was produced.

As the light guide, a fiber bundle having a length of 3 m and a diameter of 0.9 mm was used.

The light distribution angle of the light guide in a case where an end part of the light guide is in contact with the air is 85°.

Sapphire glass having a thickness of 200 μm and a diameter of 1.3 mm was used as a substrate, a holographic diffusion plate was produced on the sapphire glass by the above-described method, and a diffusion plate having a diffusion surface and a light guide unit was produced.

The holographic diffusion plate was designed so that light incident from the light guide at the above-described light distribution angle is diffused into an angle range of 100° (full angle at half maximum).

The produced diffusion plate was disposed on the end surface of the light guide such that the diffusion surface of the diffusion plate faces the end surface of the light guide. The center of the emission surface of the diffusion plate and the center of the light guide were made to match each other. As described above, an illumination optical system for endoscope was produced.

Since L is 0.2 mm and t is 200 μm (0.2 mm), t/L is 1.

[Evaluation]

The light utilization efficiency of the produced illumination unit was evaluated.

Figure 15:
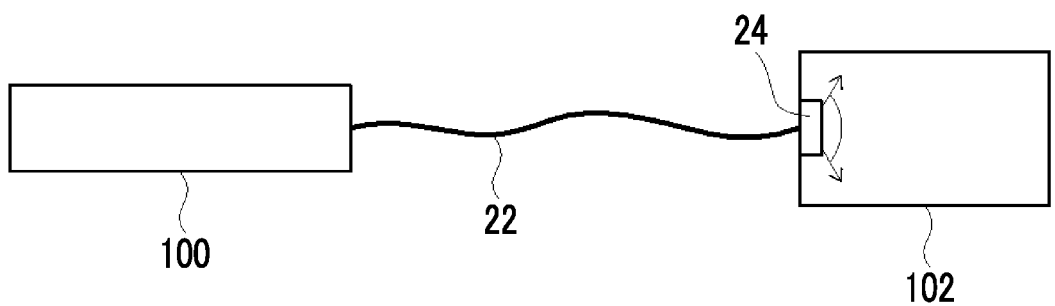
FIG. 15 is a schematic view illustrating a configuration of an evaluation system in Example.

FIG. 15 shows a schematic view of an evaluation system. The light guide 22 was connected to a xenon light source 100, the distal end of a diffusion plate 24 side was set in the light distribution measuring device, and the light utilization efficiency and the emission angular distribution were evaluated.

As a result, it was confirmed that the light utilization efficiency is high and the light irradiation angle is widened.

From the above, the effect of the present invention is clear.

EXPLANATION OF REFERENCES

10: endoscope system
12: endoscope
12a: insertion part
12b: operation part
12d: distal end portion
14: light source device for endoscope (light source device)
16: processor device
17: signal line
18: monitor
19: operational input unit
20: illumination unit
22: light guide
23: illumination optical system for endoscope
24: diffusion plate
26: light guide unit
26a: emission surface
28: diffusion surface
30: adhesive

What is claimed is:

1. An illumination optical system for endoscope which is provided in contact with an end surface of a light guide at a distal end portion of an insertion part of an endoscope, the illumination optical system for endoscope comprising:
   a diffusion plate that is provided on the end surface of the light guide and diffuses light from the light guide,
   wherein the diffusion plate has a diffusion surface that is formed on a surface on a side of the light guide and a light guide unit that guides light diffused on the diffusion surface,
   the diffusion surface consists of a holographic diffusion plate, and
   the light guide unit consists of sapphire glass.

2. The illumination optical system for endoscope according to claim 1,
   wherein an emission surface of the light guide unit on a side opposite to the diffusion surface includes the end surface of the light guide when viewed from a direction perpendicular to a surface of the light guide unit of the diffusion plate on the side opposite to the diffusion surface, and
   in a case where a shortest distance between an edge side of the emission surface and an edge side of the end surface of the light guide, in an in-plane direction of the emission surface, is denoted by L, and
   a thickness of the diffusion plate in a direction perpendicular to the emission surface is denoted by t,
   t/L≤1.6 is satisfied.

3. The illumination optical system for endoscope according to claim 2,
   wherein the shortest distance L and the thickness t satisfy 0.5≤t/L≤1.6.

4. The illumination optical system for endoscope according to claim 3,
   wherein the thickness t is 0.2 mm or more and 0.5 mm or less.

5. The illumination optical system for endoscope according to claim 3,
   wherein a diffusion angle at half maximum of the diffusion plate is 30° or more.

6. The illumination optical system for endoscope according to claim 3,
   wherein a light distribution angle of the light guide is 80° or more.

7. The illumination optical system for endoscope according to claim 3,
   wherein a side surface of the light guide unit is bonded by an adhesive or is brazed to the distal end portion of the insertion part of the endoscope.

8. The illumination optical system for endoscope according to claim 2,
   wherein the thickness t is 0.2 mm or more and 0.5 mm or less.

9. The illumination optical system for endoscope according to claim 2,
   wherein a diffusion angle at half maximum of the diffusion plate is 30° or more.

10. The illumination optical system for endoscope according to claim 2,
    wherein a light distribution angle of the light guide is 80° or more.

11. The illumination optical system for endoscope according to claim 2,
    wherein a side surface of the light guide unit is bonded by an adhesive or is brazed to the distal end portion of the insertion part of the endoscope.

12. The illumination optical system for endoscope according to claim 2,
    wherein an emission surface of the light guide unit has a circular shape when viewed from a direction perpendicular to the emission surface of the light guide unit of the diffusion plate, and
    the end surface of the light guide has a circular shape.

13. The illumination optical system for endoscope according to claim 12,
wherein the end surface of the light guide has a diameter of 0.5 mm to 2.0 mm.

14. The illumination optical system for endoscope according to claim 2,
wherein an emission surface of the light guide unit is in contact with an air layer.

15. The illumination optical system for endoscope according to claim 1,
wherein a diffusion angle at half maximum of the diffusion plate is 30° or more.

16. The illumination optical system for endoscope according to claim 1,
wherein a light distribution angle of the light guide is 80° or more.

17. The illumination optical system for endoscope according to claim 1,
wherein a side surface of the light guide unit is bonded by an adhesive or is brazed to the distal end portion of the insertion part of the endoscope.

18. The illumination optical system for endoscope according to claim 1,
wherein an emission surface of the light guide unit has a circular shape when viewed from a direction perpendicular to the emission surface of the light guide unit of the diffusion plate, and
the end surface of the light guide has a circular shape.

19. The illumination optical system for endoscope according to claim 18,
wherein the end surface of the light guide has a diameter of 0.5 mm to 2.0 mm.

20. The illumination optical system for endoscope according to claim 1,
wherein an emission surface of the light guide unit is in contact with an air layer.

21. An endoscope comprising:
the illumination optical system for endoscope according to claim 1, which is provided in contact with the end surface of the light guide at the distal end portion of the insertion part of the endoscope, and
an image pick-up unit that picks up an observation site irradiated with illumination light with the illumination optical system for endoscope.

* * * * *